US009586921B2

(12) United States Patent
Yamamoto et al.

(10) Patent No.: US 9,586,921 B2
(45) Date of Patent: Mar. 7, 2017

(54) BURDOCK FRUIT EXTRACT CONTAINING ARCTIGENIN AT HIGH CONTENT AND PROCESS FOR PRODUCING SAME

(75) Inventors: Keiichi Yamamoto, Toyama (JP); Toshiki Okubo, Toyama (JP); Satoshi Yomoda, Toyama (JP); Hiroyasu Esumi, Chiba (JP); Chika Miyoshi, Chiba (JP); Shigetoshi Kadota, Toyama (JP)

(73) Assignees: Kracie Pharma, Ltd., Minato-ku (JP); Japan as Represented by President of National Cancer Center, Chuo-Ku (JP); National University Corporation University of Toyama, Toyama-shi (JP)

( * ) Notice: Subject to any disclaimer, the term of this patent is extended or adjusted under 35 U.S.C. 154(b) by 35 days.

(21) Appl. No.: 13/260,506

(22) PCT Filed: Feb. 5, 2010

(86) PCT No.: PCT/JP2010/051701
§ 371 (c)(1),
(2), (4) Date: Sep. 26, 2011

(87) PCT Pub. No.: WO2010/109961
PCT Pub. Date: Sep. 30, 2010

(65) Prior Publication Data
US 2012/0029070 A1  Feb. 2, 2012

(30) Foreign Application Priority Data
Mar. 27, 2009 (JP) ................................. 2009-079590

(51) Int. Cl.
| *A61K 31/365* | (2006.01) |
| *C07D 307/33* | (2006.01) |
| *A61K 9/16* | (2006.01) |
| *A61K 9/20* | (2006.01) |
| *A61K 36/28* | (2006.01) |
| *A61K 9/19* | (2006.01) |

(52) U.S. Cl.
CPC .......... *C07D 307/33* (2013.01); *A61K 9/1623* (2013.01); *A61K 9/1688* (2013.01); *A61K 9/2054* (2013.01); *A61K 31/365* (2013.01); *A61K 36/28* (2013.01); *A61K 9/19* (2013.01)

(58) Field of Classification Search
CPC .................................................. A61K 9/1623
See application file for complete search history.

(56) References Cited

U.S. PATENT DOCUMENTS 8,067,036 B2 * 11/2011 Kato ..................... A23L 1/3002
424/725

FOREIGN PATENT DOCUMENTS

| CN | 1 560 265 A | | 1/2005 |
| CN | 1560265 A | * | 1/2005 |
| CN | 1569138 | * | 1/2005 |
| CN | 1569138 A | | 1/2005 |
| CN | 1864705 | * | 11/2006 |
| CN | 1864705 A | | 11/2006 |
| CN | 101036644 A | | 9/2007 |
| CN | B101036644 | * | 9/2007 |
| CN | 101 358 173 A | | 2/2009 |
| CN | 101358173 A | | 2/2009 |
| CN | 101358173 A | * | 2/2009 |
| EP | 0930019 A2 | | 7/1999 |
| JP | 11-187843 A | | 7/1999 |
| JP | 2008-255083 A | | 10/2008 |
| JP | 2008-2550838 A | * | 10/2008 |
| JP | 2008255083 A | | 10/2008 |

OTHER PUBLICATIONS

Duh JAOCS, 1998, 75(4):455-461.*
Kardosova et a. International J of Biological Macromolecules, 2003, 33:135-140.*
Notification of Reasons for Rejection for Japanese Patent Application 2010-505497 issued Nov. 21, 2011.
Extended European Search Report for EP201075576, Jul. 5, 2012.
Han, B. H. et al., A Butyrolactone Lignan Dimer from Arctium Lappa, Phytochemistry, 1994, vol. 37, No. 4, p. 1161-1163.
Xu, Fei-yi et al., Studies on Microbial Transformation of Fructus arctii, Nat. Prod. Res. Dev., 2007, vol. 19, No. 4, pp. 595-598 (translation of Abstract only).
Umehara, K. et al., Studies on Differentiation-Inducers from Arctium Fructus, Chem. Pharm. Bull., 1993, vol. 41, No. 10, pp. 1774-1779.
International Search Report from PCT/JP2010/051701 (parent application).
International Search Report for International Application No. PCT/JP2010/051701 mailed Apr. 20, 2010.

* cited by examiner

*Primary Examiner* — Bin Shen
(74) *Attorney, Agent, or Firm* — Locke Lord LLP; NIcholas J. DiCeglie, Jr.

(57) ABSTRACT

PROBLEM TO BE SOLVED
A burdock fruit extract containing arctigenin at high content and its production method are provided, and both of which are used for treatment of pancreatic cancer.
SOLUTION
The burdock fruit extract containing arctigenin at high content by enzymatically converted arctiin into arctigenin with beta-glucosidase, which is an enzyme occurring endogenously in a burdock fruit, and adding ethanol, extracting, concentrating and then freeze-drying or spray drying.

2 Claims, 5 Drawing Sheets

Figure 1:
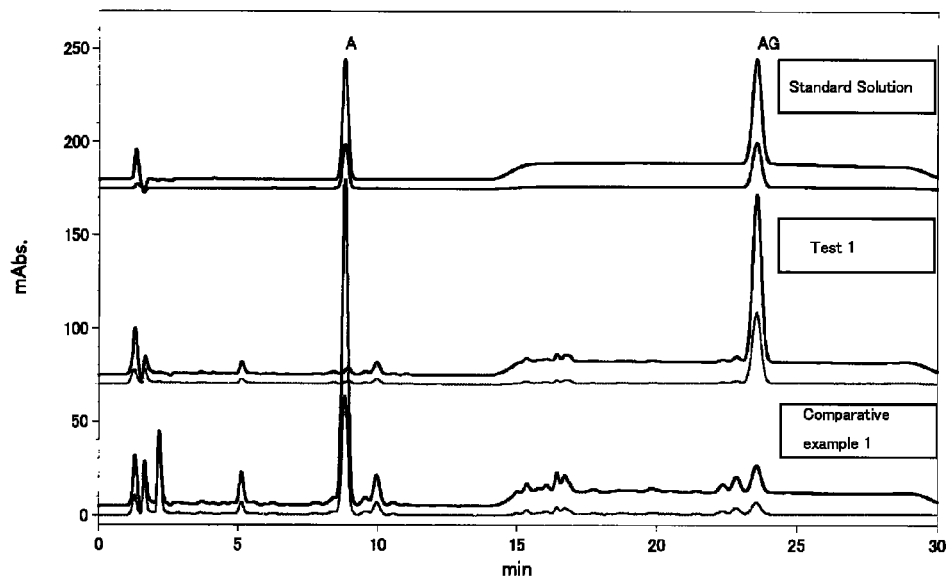

BURDOCK FRUIT EXTRACT CONTAINING ARCTIGENIN AT HIGH CONTENT AND PROCESS FOR PRODUCING SAME

CROSS-REFERENCE TO RELATED APPLICATION

This application is the U.S. national phase application, pursuant to 35 U.S.C. §371, of PCT international application Ser. No. PCT/JP2010/051701, filed Feb. 5, 2010, designating the United States, which claims the benefit of Japanese Application No. 2009-079590, filed on Mar. 27, 2009. The entire contents of the aforementioned patent applications are incorporated herein by this reference.

FIELD OF THE INVENTION

The present invention relates to a burdock fruit extract containing arctigenin at high content and process for extracting and producing same.

BACKGROUND ART

In the Japanese Pharmacopeia 15th edition, a burdock fruit is defined as a fruit of burdock, *Arctum lappa* Linne (Compositae), which is herbal medicine prescribed for Gingyo-san, Kufugedoku-to, Shofu-san and the like, and which is classified in the primary material to be used as pharmaceutical agent exclusively.

A burdock fruit contains approximately 7% of arctiin which is classified in lignan glycoside and approximately 0.6% of arctigenin which is an aglycone of arctiin.

In recent years, the cells derived from pancreas cancer such as PANC-1, AsPC-1, BxPC-1 and KP-3 have strong tolerance to the extreme nutrition fasting state, and the possibility is reported that the elimination of the tolerance becomes a new biochemical approach in the cancer therapy (patent document 1).

In addition, it is reported that arctigenin is effective, when screened a material which could release the viability of tumor cells in the undernutrition condition using pancreas cancer cell line PANC-1 (non-patent document 1).

PRIOR ART DOCUMENT

Patent Document

Patent document 1: Japanese Kokai Publication No. 2002-065298

Non-Patent Document

Non-patent document 1: S. Awale, J. Lu, S. K. Kalauni, Y. Kurashima, Y. Tezuka, S. Kadota, H. Esumi, Cancer Res., 2006, 66(3), 1751-1757)

SUMMARY OF THE INVENTION

Problem to be Solved by the Invention

The known burdock fruit contains arctigenin at low content with approximately 0.6%, and it is hard to dissolve in water. Thus, it is extremely difficult to produce the extract containing arctigenin at high content by a conventional hot water extraction method.

Therefore, it has been desired that the burdock fruit extract, which has the form which can be actually administered to the living body, and which contains arctigenin at high content, is provided.

Thus, the problem of the present invention is to provide a burdock fruit extract containing arctigenin at high content and process for producing same.

Means to Solve the Problem

As a result of the diligent investigation in order to solve the problem, the inventors focused on a beta-glucosidase which was the enzyme inherent in herbal medicine, and they found a technique to convert arctiin into arctigenin using the reaction by this enzyme, a technique to extract the converted arctigenin efficiently, and a burdock fruit extract containing arctigenin at high content.

The first invention is a burdock fruit extract containing arctigenin at high content with more than 3% of arctigenin.

The second invention is a method for producing a burdock fruit extract containing arctigenin at high content, comprising converting arctiin into arctigenin by enzymatic conversion by the beta-glucosidase which is inherent in herbal medicine, and extracting arctigenin.

The third invention is a method for producing a burdock fruit extract containing arctigenin at high content, comprising extracting by adding ethanol after converting arctiin into arctigenin by the enzymatic conversion in any of the invention.

The fourth invention is a method for producing a burdock fruit extract containing arctigenin at high content, comprising concentrating and freeze-drying or spray drying for production after the extraction in any of the invention.

The fifth invention is a method for producing a burdock fruit extract containing arctigenin at high content, comprising concentrating, adding dextrin and spray drying after the extraction in any of the invention.

Effect of the Invention

A burdock fruit extract containing arctigenin at high content which have an antitumor effect can be provided according to the present invention. An effect on the growth inhibition of the tumor and the antitumor effect can be expected by administering to a patient with the pancreas cancer in particular. Moreover, the productivity can be improved when produce.

BRIEF DESCRIPTIONS OF THE DRAWINGS

Figure 2:
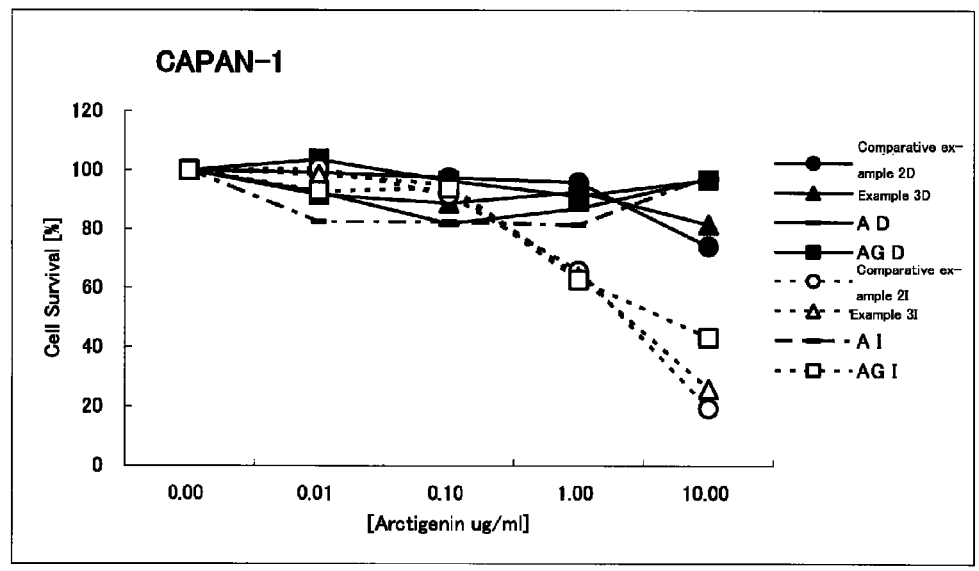

FIG. 1 Chromatogram analysis of results of the efficacy of the enzymatic conversion FIG. 2 Evaluation of the cytotoxicity using the culture cell (CAPAN-1)

Figure 3:
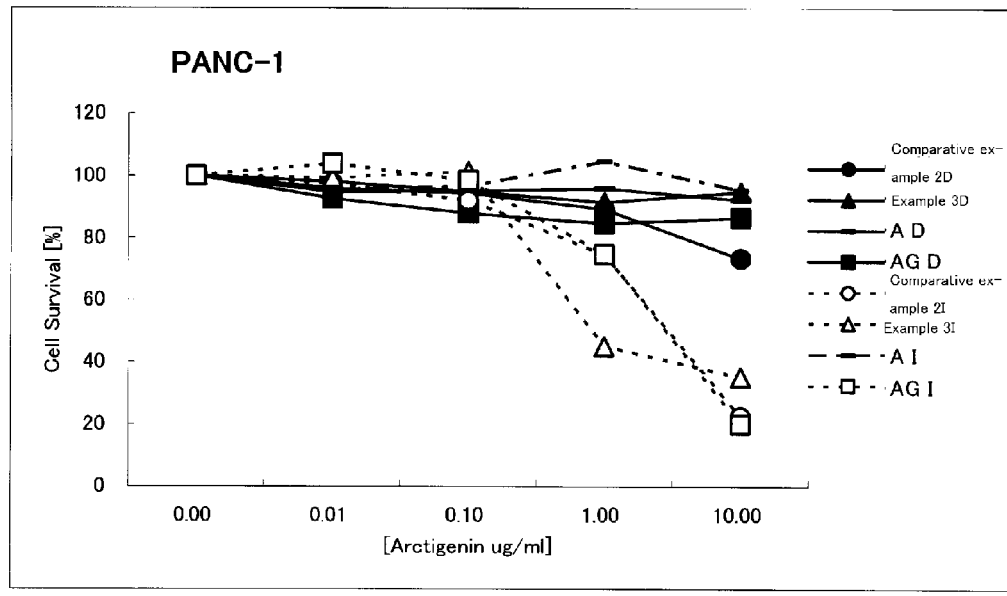

FIG. 3 Evaluation of the cytotoxicity using the culture cell (PANC-1)

Figure 4:
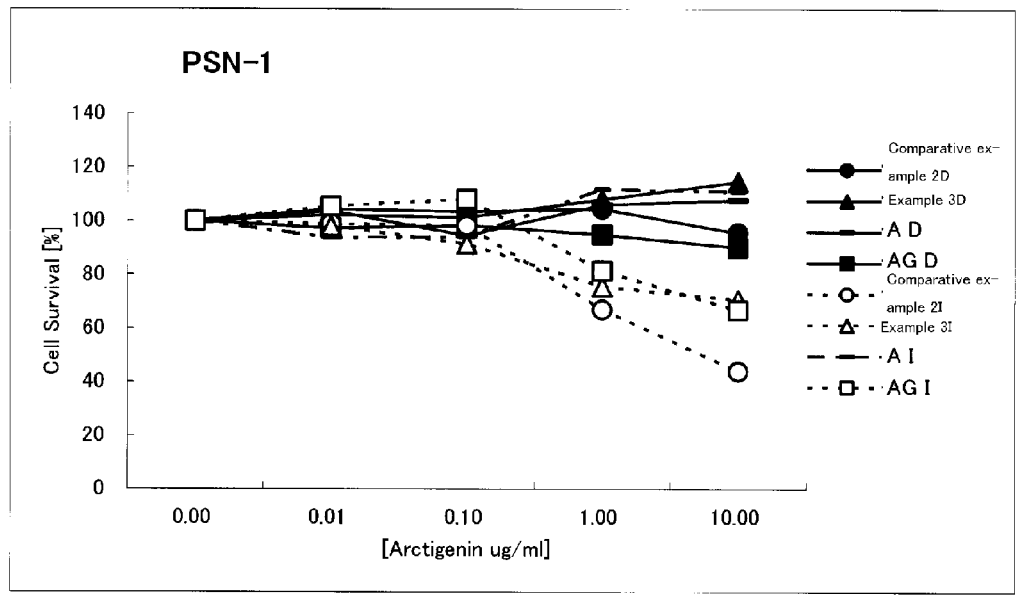

FIG. 4 Evaluation of the cytotoxicity using the culture cell (PSN-1)

Figure 5:
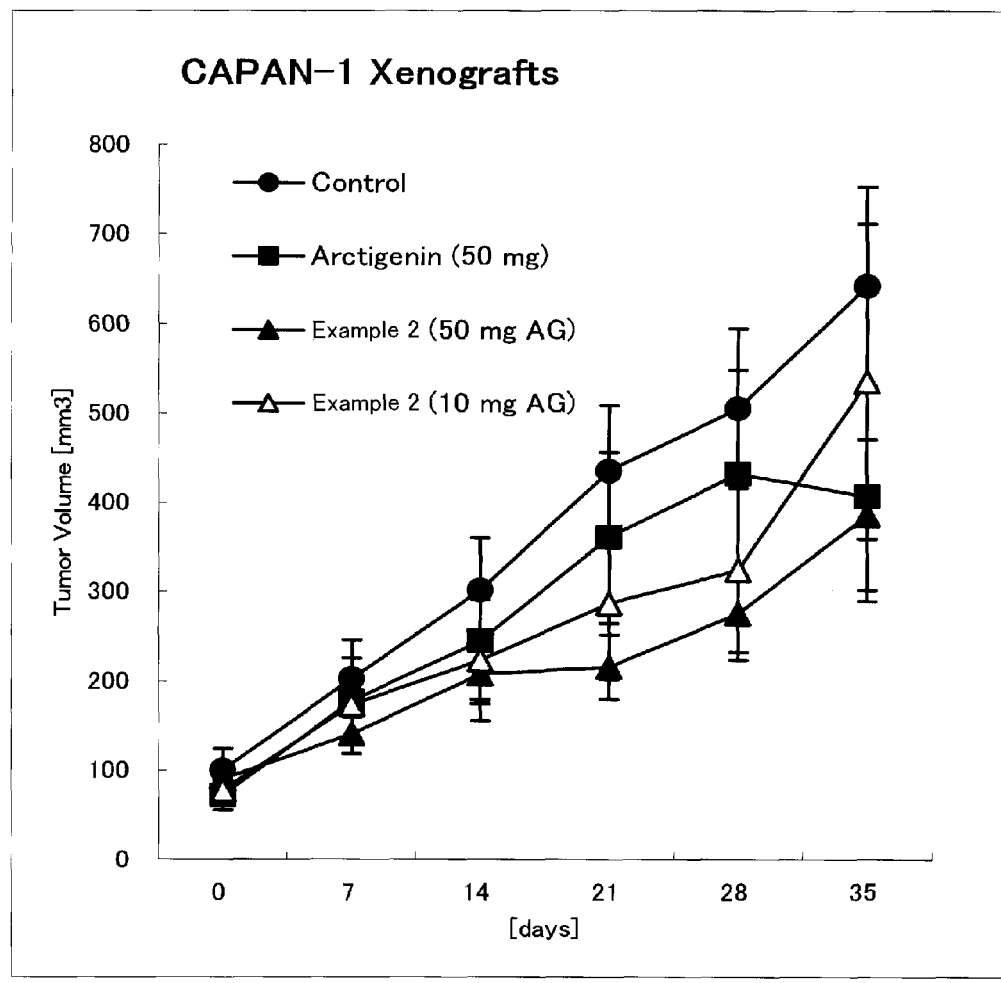

FIG. 5 Evaluation of the anticancer activity in the animal model of a tumor (CAPAN-1 Xenografts)

Figure 6:
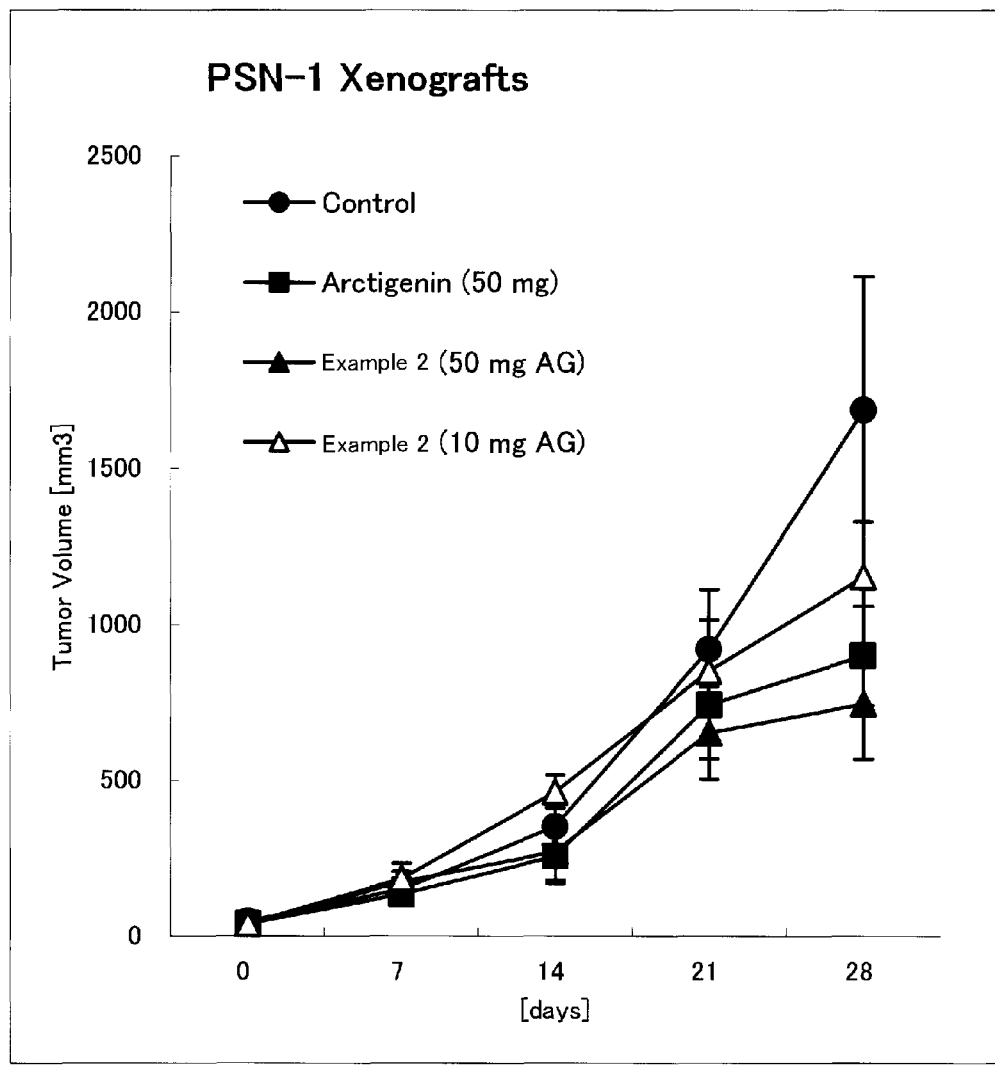

FIG. 6 Evaluation of the anticancer activity in the animal model of a tumor (PSN-1 Xenografts)

Figure 7:
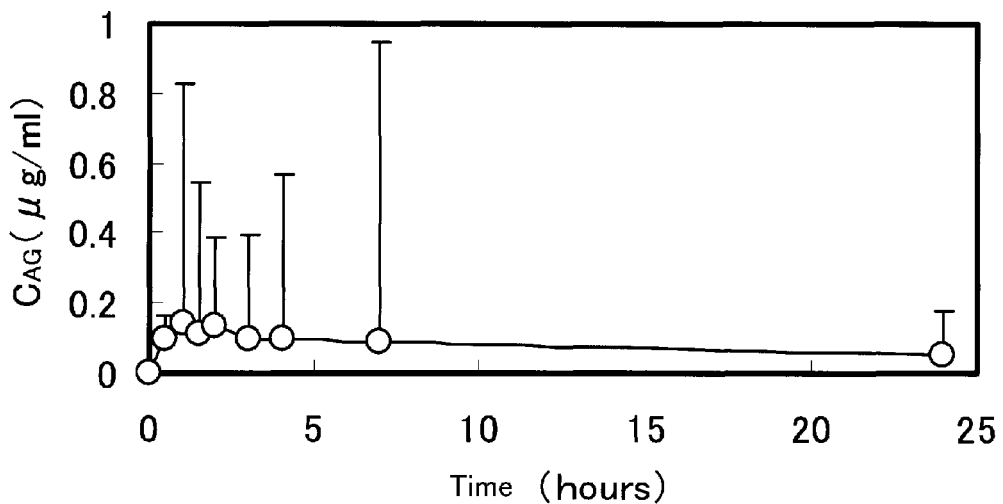

FIG. 7 Change of the blood concentration of the human blood arctigenin (AG)

Figure 8:
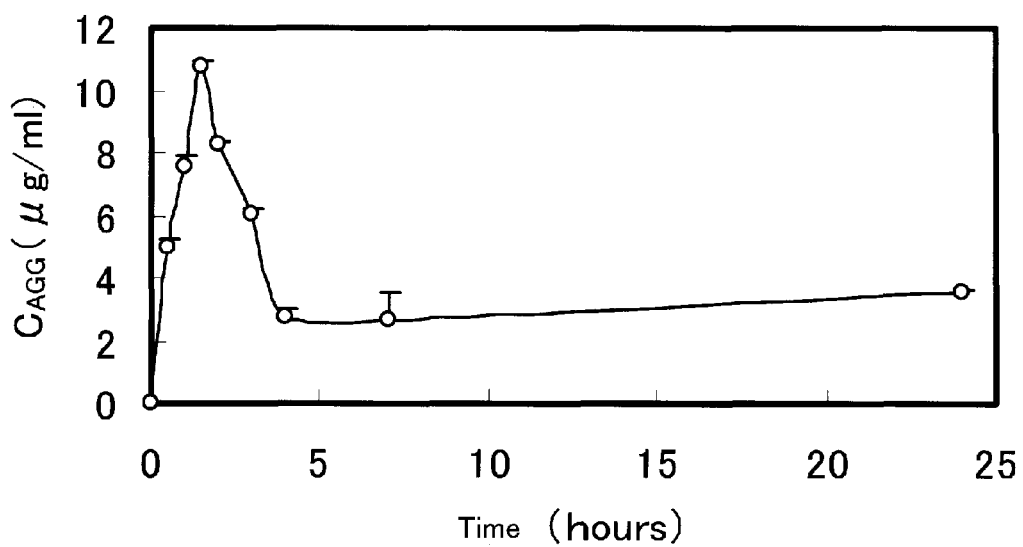

FIG. 8 Change of the blood concentration of the human blood arctigenin-glucuronic acid conjugate (AGG)

EMBODIMENT FOR CARRYING OUT THE INVENTION

The present inventions are described below in detail. The disclosed conditions are an example, and not limited to this.

A burdock fruit extract of the present invention is produced through steps of cutting a herbal medicine, extracting, separating a solid-liquid, concentrating and drying.

(The Step of Cutting the Herbal Medicine)

The burdock fruit which is a source is cut into the size suitable for the extraction. The herbal medicine which is a source is one of various areas of plants, minerals, animals and the like, which have various kinds of size, a shape and a hardness, so that it is necessary to cut it depending on its property. When grain size is small, enzyme reaction is promoted and a yield of the extract is rised, but on the other hand, the enzyme reaction become too quick and a process control becomes difficult, and a hindrance may occur in the accurate solid-liquid separation in post-process. Therefore, chopping is desirable for the grain size of the herbal medicine as used herein.

(The Step of Extracting)

The step of extracting is the most important step in the steps of producing the powder of Chinese medicine extract for a quality, and this step decides a quality of the powder of Chinese medicine. In the present invention, the step of extracting is carried out in two stages of an enzyme reaction step and an organic solvent extraction step.

(The Step of the Enzyme Reaction)

It is the most important step found in the present invention, and it is the step to convert enzymatically arctiin contained in a burdock fruit into arctigenin.

7 liters of water is added to 1 kg of the chopped burdock fruit prepared in a previous step, and stand for approximately one hour, for example, at 20-40° C. under agitation. Arctiin is converted into arctigenin by enzymatic conversion in this step, and content of arctigenin rises drastically. The extracting method is called enfleurage extraction.

Note that, in the point of view of the rate of the reaction, 37-40° C. that is peak temperature of the enzymatic reaction is desirable, but because rate of reaction is too fast at this temperature, a process control may become difficult in the point of view of the quality control.

Thus, it is desirable to extract at 20-25° C. for approximately one hour in the small scale, but on the other hand, in the industrial scale, it should be set appropriately at 30° C. for 30 minutes, at 37° C. for 15 minutes or the like depending on the ability of the stirrer and the ability of the temperature control. Note that, the conventional hot water heating method which becomes the further temperature cannot be used, because the enzyme deactivates at the temperature more than 60° C.

(The Step of the Organic Solvent Extraction)

It is the step to heat to reflux in the condition where arctigenin became the high content, and to extract the burdock fruit extract. Here, the yield can be improved by adding solvent, because arctigenin has low water solubility.

Specifically, to the solution after the step of the enzymatic reaction (1 kg of the chopped burdock fruit+7 liters of water), 3 liters of the solvent is added, and heated to reflux for another one hour. Here, ethanol is desirable for the solvent for safety.

The solubility of arctigenin becomes higher and the yield is improved as the quantity of ethanol increases, but a lot of unnecessary oils and fats begin to be melt and the load on the concentrating step grows big, thus the quantity to be added should be decided depending on the situation appropriately. Note that the heating to reflux in the process of serves as the sterilization.

(The Step of Separating Solid-Liquid)

It is a step to separate the herbal medicine used for extraction from the extract. Solid-liquid separation methods include a filtration method, a sedimentation method and the like, and the method by a centrifugal separation is desirable industrially.

(The Step of Concentration)

It is a step to remove the solvent in the extract prior to drying. A vacuum concentration method is used, such that the obtained extract is no longer exposed to high temperature for a long time. In this step, it is concentrated to the concentration where the drying of the next step can be performed appropriately and the appropriate properties of the preparation can be provided when the dried extract powder is prepared.

Note that, a large amount of arctigenin is adhered within a manufacturing apparatus used in the drying step, and a final yield is significantly reduced, because arctigenin has low water solubility. Thus, the adhesion to the manufacturing apparatus can be prevented by adding dextrin. Around 20% are desirable for the quantity of its addition to a solid of the concentrate.

(The Step of Drying)

It is a step to finish the extracted extract in the shape of powder. Freeze-drying and spray drying are known for a drying method, and it is common to use the former if it is a laboratory level and the latter if it is a mass production level.

The burdock fruit extract containing arctigenin at high content can be obtained by the above mentioned steps of manufacturing.

(Combination Preparation of the Burdock Fruit Extract Powder)

The powder of the extract thus obtained can be used in the form without being processed, and also in the form of the granulated substance which is usually produced by adding general diluting agent (e.g., crystalline cellulose, sucrose fatty acid ester, lactose) used for food and/or pharmaceutical agent to the extract powder, and for example, granulating by dry granulating or wet granulation without further processing or with further compression molding using a tablet machine.

Moreover, a preparation in which the powder of the extract is masked is preferable for dosage, and it may be the film coating agent coated with a coating agent, because the powder of the extract has special acrid taste. Moreover, the above mentioned powder of the extract or the granulated substance may be filled into a hard capsule or a soft capsule and be taken, from the viewpoint of the stability of the ingredient and easiness of the intake.

(Examination) Examination on the Efficacy of the Enzymatic Conversion for Arctigenin In the step of the enzymatic reaction (enfleurage extraction) of the step of the extraction, whether or not arctiin was converted into arctigenin by enzymatic conversion was examined.

Comparative Example 1

0.1 g of the coarse powder of the burdock fruit (18 sieve passed) is taken, 50 mL of the 50% methanol is added and after heating for one hour, filtered.

[Test 1] 0.1 g of the coarse powder of the burdock fruit (18 sieve passed) is taken, 25 mL of water is added and mixed by shaking, and after standing it in room temperature (20° C.) for one hour, 25 mL of the methanol is added and filtered Each concentrate obtained with comparative example 1 and test 1 were measured by the HPLC method in the following aSolution

[Arctigenin Content Measuring Method]

A column: YMC-Pack ProC18 AS-307-3 (3 μm, 4.6 mmID*7.5 cm)

Column temperature: 30° C.

Detection: UV280 nm (the upper section), UV230 nm (the lower section)

Flow rate: 0.8 mL/min

Quantity to inject: 5, 10 μL

Mobile phase: A liquid/0.05M sodium dihydrogen phosphate solution:acetonitrile mixed solution (5:1), B liquid/0.05M sodium dihydrogen phosphate solution:acetonitrile mixed solution (1:1)

Gradient condition: 0-10 min/20% B liquid, 10-25 min/40% B liquid

Comparative Example 1

As shown in Table 1, the content of arctiin and the content of arctigenin in the raw materials of the herbal medicine were 6.88% and 0.58%, respectively, and the ratio of arctigenin/arctiin of the content (hereinafter, referred to AG/A) was 0.08.

[test 1] As shown in Table 1, the content of arctiin and the content of arctigenin were 0.15% and 3.80%, respectively, and the AG/A ratio was 25.33, and arctigenin content was increased clearly. Moreover, as shown in FIG. 1, arctiin in the raw materials of the herbal medicine converted into arctigenin approximately quantitatively.

TABLE 1

| | Grain size of the herbal medicine of raw materials | Process of the enzymatic conversion | Content of arctiin (%) | Content of arctigenin (%) | AG/A ratio |
|---|---|---|---|---|---|
| Comparative example 1 | Coarse powder | No | 6.88 | 0.58 | 0.08 |
| Test 1 | Coarse powder | Yes (22° C.) | 0.15 | 3.80 | 25.33 |

EXAMPLES

Example 1

Production of the Burdock Fruit Extract by Mincing and Enfleurage Extraction 300 g of the chopped burdock fruit was added to 1.5 L of water (22° C.), stirred for one hour, and then further heated to reflux for one hour. Likewise, it was filtered and washed by 0.5 L of water, and the combined extract (1.5 L) was freeze-dried.

As shown in Table 2, the content of arctiin and the content of arctigenin in the extract of the minced herbal medicine by enfleurage extraction were 10.1% and 4.8%, respectively, and the AG/A ratio was 0.48.

Example 2

Production of the Burdock Fruit Extract by Mincing, Enfleurage Extraction and Ethanol Addition 200 g of the chopped burdock fruit was added to 1 L of water (22° C.), stirred for one hour, and after 0.45 L of ethanol was added, and further heated to reflux for one hour. It was filtered by four pieces of gauze (gauze 100 mesh) and washed by 0.5 L of 30% ethanol, and the combined extract (1.5 L) was freeze-dried.

As shown in Table 2, the content of arctiin and the content of arctigenin in the extract of the minced herbal medicine by enfleurage extraction were 13.3% and 11.4%, respectively, and the AG/A ratio was 0.86. The content of arctigenin significantly increased than Example 1, and it is supposed that arctigenin was able to be dissolved by adding ethanol.

Examples 3-6

Production of the Burdock Fruit Extract by Middle Scale, Spray Drying 2 kg of the chopped burdock fruit was added to 14 L of water (37° C.), stirred for one hour, and then 6 L of ethanol was added, and further heated to reflux for one hour. This solution was centrifuged, approximately 16 L of the obtained extract was concentrated by vacuum concentration, and added dextrin which was 0-50% against the solid of the extract and dried by spray drying.

A lot of arctigenin was lost by the adhesion in a spray drying step, because arctigenin is hard to dissolve in water, and the yield of the extract fell to 5% (Example 3).

Thus, the adhesion to a machine was prevented by adding of the dextrin (Examples 3-6), and the spray dried extract superior in fluidity was able to be prepared. The yield of the extract was improved from 5% to around 20%.

In respect to the added quantity, it is desirable to add around 20% against the solid of the concentrate.

Example 7

Production of the Burdock Fruit Extract by Middle Scale, Spray Drying 2 kg of the chopped burdock fruit was added to 14 L of water (22° C.), stirred for one hour, and then 6 L of ethanol was added, and further heated to reflux for one hour. This solution was centrifuged, approximately 16 L of the extract obtained was concentrated by vacuum concentration, and added dextrin which was 20% against the solid of the extract, and dried by spray drying.

The content of arctiin and the content of arctigenin were 7.1% and 6.3%, respectively, and the AG/A ratio became 0.89, thus, the results of the laboratory was able to be reproduced, and a large quantity of the extract was obtained.

Example 8

Production of the Burdock Fruit Extract by Industrial Scale, Spray Drying 80 kg of the chopped burdock fruit was added to 560 L of water which was warmed to 30° C. and after stirring for 30 minutes, 265 L of ethanol was added and increased a temperature to 85° C., and further heated and extracted for 30 minutes. This solution was centrifuged and the extract was obtained. This procedure was repeated twice, and the obtained extract were combined and concentrated in vacuum, and added dextrin which was 20% against the solid of the extract, and dried by spray drying.

The content of arctiin and the content of arctigenin were 6.8% and 5.9%, respectively, and the AG/A ratio became 0.87, thus, the results of the middle scale could be reproduced, and 31.5 kg of the powder of the extract (containing 20% dextrin) was obtained.

Comparative Example 2

Production of the Burdock Fruit Extract by Mincing, Hot Water Extraction 300 g of the chopped burdock fruit (8.6 passage) was added to 1.5 L of the hot water (80° C.) and after heated to reflux for one hour, it was filtered by four pieces of gauze (gauze 100 mesh) while heating. It was washed by 0.5 L of water and the combined extract (1.4 L) was freeze-dried.

The content of arctiin and the content of arctigenin, which was obtained from the herbal medicine of the raw materials by heating extraction using water as a solvent for extraction as usually performed, were 29.2% and 0.92%, respectively, and the AG/A ratio was 0.03. The AG/A ratio was further decreased, confirming arctigenin is hard to move to extract.

granular, and each of 1.5 g were wrapped by laminated film of aluminum, and thereby the granule of Example 9 which contained 0.5 g of burdock fruit extract powder per one package was obtained.

Example 10

Combined Tablet of Burdock Fruit Extract

| | |
|---|---|
| (1) powder of the burdock fruit extract of Example 8 | 37.0% |
| (2) crystalline cellulose | 45.1% |
| (3) carmellose calcium | 10.0% |
| (4) crospovidone | 3.5% |
| (5) hydrous silicon dioxides | 3.4% |
| (6) magnesium stearate | 1.0% |
| total | 100% |

(Method for Production)

The tablets are produced based on the paragraph of the tablet of the general rules for preparations of "the Japanese Pharmacopoeia". That is, the ingredients from the powder of the burdock fruit extract to the magnesium stearate described in the above list were taken, and the tablet of Example 10 was obtained.

TABLE 2

| | Grain size of the herbal medicine of the raw materials | Process of the enzymatic conversion | Extraction by ethanol | Addition of the dextrin | Yield of the extract (%) | Content of arctiin (%) | Content of arctigenin (%) | AG/A ratio |
|---|---|---|---|---|---|---|---|---|
| Example 1 | Chopped | Yes (22° C.) | No | No | 10.9 | 10.1 | 4.8 | 0.48 |
| Example 2 | Chopped | Yes (22° C.) | Yes | No | 19.1 | 13.3 | 11.4 | 0.86 |
| Example 3 | Chopped | Yes (37° C.) | Yes | No | 5.0 | 6.3 | 11.2 | 1.78 |
| Example 4 | Chopped | Yes (37° C.) | Yes | Yes (15%) | 17.1 | 4.3 | 11.5 | 2.67 |
| Example 5 | Chopped | Yes (37° C.) | Yes | Yes (25%) | 19.6 | 4.0 | 10.7 | 2.68 |
| Example 6 | Chopped | Yes (37° C.) | Yes | Yes (50%) | 21.0 | 2.7 | 10.8 | 4.00 |
| Example 7 | Chopped | Yes (22° C.) | Yes | Yes (20%) | 19.0 | 7.1 | 6.3 | 0.89 |
| Example 8 | Chopped | Yes (30° C.) | Yes | Yes (20%) | 15.8 | 6.8 | 5.9 | 0.87 |
| Comparative example 2 | Chopped | No | No | No | 11.3 | 29.2 | 0.9 | 0.03 |

Example 9

Combined Granule of Burdock Fruit Extract

| | |
|---|---|
| (1) powder of burdock fruit extract of Example 8 | 33.3% |
| (2) lactose | 65.2% |
| (3) hydroxypropylcellulose | 1.5% |
| total | 100% |

(Method for Production)

The granules are produced based on the paragraph of the granule of the general rules for preparations of "the Japanese Pharmacopoeia". That is, the ingredients from the powder of the burdock fruit extract to the hydroxypropylcellulose described in the above list were taken, and they were made

[Test 2] (Cytotoxic Evaluation Using the Cultured Cell)

(Method for Test)

The pancreas cancer cell line, CAPAN-1, PANC-1 and PSN-1 were plated to the 96 well plate, and they were pre-cultured in DMEM culture media in 37° C., 5% CO2 and 95% Air under normal nutritional condition for 24 hours. After washing these cells with PBS, the extracts which were extracted by the different methods in DMEM culture media (ending D in the graph) which is normal nutritional condition and in NDM culture media (ending I in the graph) which are a nutrient starvation condition (Example 2 and comparative example 2 in the graph) were added to each well including constant concentration of arctigenin, and incubated for 24 hours. The cells were washed in PBS again, 100 μL of DMEM culture media including 10% WST-8 was added to be reacted for two hours and measured the absorbance of 450 nm by the microplate reader, and viability of these cells were evaluated.

As a result of the evaluation, as shown in FIGS. 2-4, the burdock fruit extract showed the remarkable and selective cytotoxicity to either pancreas cancer cell lines in culture media under nutrient starvation. Moreover, it became clear that the extract also had the antitumor effect depending on the concentration of arctigenin and the effect was equal to purified arctigenin. Furthermore, the anticancer activity was found by arctiin (in the graph: A) which was a precursor of arctigenin (in the graph: AG) in neither condition.

[Test 3] (the Evaluation of the Anticancer Activity in the Model Animal of Tumor)

(Method for Test)

The subcutaneous dorsales of nude mouse (BALB-cAJ nu/nu; Nippon Kurea) which is the donor was inoculated the human pancreas cancer cell line, CAPAN-1 or PSN-1, and the obtained tumor mass of the donor mouse was transplanted into the subcutaneous dorsales of the recipient mouse to generate the model animal of tumor. Arctigenin (AG), arctiin (A) and the burdock fruit extract (Example 2) dissolved in DMSO with the concentration of 10 mg/mL were diluted with saline and 50 μg of them per mouse was intragastrically administered by mouth five times a week. The anticancer activity was evaluated by measuring the size of the tumor mass of subcutaneous dorsales sequentially.

One month after the beginning of the dosage, the remarkable effect for depressing the growth of the tumor in the group administered the agent compared to the control. The antitumor effect was also obtained in the group administered the purified arctigenin, however the stronger antitumor effect was found by the burdock fruit extract (Example 2) containing arctiin which was a precursor (FIGS. 5 and 6).

[Test 4] (Blood Concentration)

(Method for Test)

With one healthy male volunteer who was a subject, after dosage of two packages of the granules of Example 9 (1 g of the burdock fruit extract powder), approximately 5 mL of the blood was collected from his vein sequentially (at 30 minutes before dosage, and at 0.5 hours, 1 hour, 1.5 hours, 2 hours, 3 hours, 4 hours and 7 hours after dosage), and the plasma sample was obtained. To 500 μL of the plasma sample thus obtained, 500 μL of solution of 0.1 mol/L sodium dihydrogen phosphate and 100 μL of solution of the internal standard (IS) were added. This was transferred to a test tube, and 6 mL of the methanol was added, and centrifuged after mixed by shaking, and the methanol layer was taken and dryed to solid in vacuum, and 250 μL of 70% acetonitrile was added to the residue to give the sample solution. This was measured by the high performance liquid chromatography (HPLC) method using the following conditions, and calculated the concentration of arctigenin (AG) and the concentration of glucuronic acid conjugate of arctigenin (AGG), respectively from ratio of the peak height to the internal standard substance.

(HPLC Condition)

A column: YMC-packODS-A-312

Mobile phase: hydrogen sodium solution in 0.1 mol/L phosphoric acid including 0.2% phosphoric acid/acetonitrile mixed solution (73.5:26.5)

Column temperature: 40° C.

Flow rate: 1.0 mL/min

Detection: UV210 nm

Quantity to inject: 10 μL

Internal Standard Solution 10 mg of 4-hydroxybenzoic acid isopropyl is dissolved in 50% methanol to become 50 mL, and 50% methanol is added to 1 mL of this solution to become 100 mL, and give an internal standard solution.

(Results of the Test)

Change of the concentration of AG and AGG in the human plasma were shown in FIGS. 7 and 8, respectively. As is apparent from FIGS. 7 and 8, the main ingredient detected in the blood by the intake of the powder of the burdock fruit extract of the present invention was AGG. For the blood concentration of AG ($C_{AG}$), bimodal peaks were detected at one hour and two hours, and the maximum concentration (Cmax) was 0.15 μg/mL. Moreover, it is conceivable that there is the influence by the intestines—liver circulation, because the elimination from the blood was slow. For the blood concentration of AGG ($C_{AGG}$), the peak was recognized at 1.5 hours, and Cmax was 10.7 μg/mL. Moreover, the elimination from the blood was also slow with 3.6 μg/mL after 24 hours, so that influence by the intestines—liver circulation is considered similarly. Thus, the in vivo effect can be expected by the intake of the powder of the burdock fruit extract of the present invention, because the AG and AGG levels were maintained in the blood for a long time.

What is claimed is:

1. A method for producing an extract from burdock fruit, said extract containing arctigenin at a high content of more than 3% of arctigenin, comprising the steps of:
    a) cutting a burdock fruit;
    b) adding water to said burdock fruit;
    c) agitating said burdock fruit in water at a temperature of 20-60° C., thereby converting arctiin in said burdock fruit into arctigenin by enzymatic conversion using beta-glucosidase, wherein said beta-glucosidase consists of endogenous beta-glucosidase that is inherently present in said burdock fruit used in herbal medicine;
    d) adding ethanol to the burdock fruit in water after the agitating step c) to form a solution comprising a burdock fruit extract;
    e) obtaining the burdock fruit extract from the solution; and
    f) concentrating and freeze-drying or spray drying the burdock fruit extract after the obtaining step e) to produce an extract from burdock fruit containing arctigenin at a high content of more than 3% of arctigenin.

2. The method for producing burdock fruit extract containing arctigenin at high content as claimed in claim 1 further comprising, in the step f), adding dextrin to the burdock fruit extract after concentrating and spray drying after the extraction the burdock fruit extract.

* * * * *